United States Patent [19]

Harvey et al.

[11] Patent Number: 4,757,707
[45] Date of Patent: Jul. 19, 1988

[54] MOLTEN METAL GAS ANALYSIS

[75] Inventors: David S. Harvey, Rotherham; David T. Wilson, Worrall, both of England

[73] Assignee: British Steel Corporation, England

[21] Appl. No.: 26,692

[22] Filed: Mar. 17, 1987

[30] Foreign Application Priority Data

Mar. 19, 1986 [GB] United Kingdom ................. 8606766

[51] Int. Cl.$^4$ ............................................. G01N 27/18
[52] U.S. Cl. ....................................................... 73/19
[58] Field of Search ................... 73/19, 1 G, DIG. 9, 73/27 R

[56] References Cited

U.S. PATENT DOCUMENTS

| | | | |
|---|---|---|---|
| 3,451,256 | 6/1969 | Kolodney | 73/19 X |
| 3,941,566 | 3/1976 | Roche | 73/19 X |
| 4,143,316 | 3/1979 | Roy et al. | 73/19 X |
| 4,454,748 | 6/1984 | Terai et al. | 73/19 |

FOREIGN PATENT DOCUMENTS

| | | | |
|---|---|---|---|
| 1474360 | 2/1967 | France | 73/19 |
| 684865 | 12/1952 | United Kingdom | 73/19 |
| 1004816 | 3/1983 | U.S.S.R. | 73/19 |

OTHER PUBLICATIONS

Degréve, F., New Methods for Determining $H_2$ Content in Al and its Alloys, Journ. of Metals, vol. 27(3), pp. 21–26, Mar. 1975.

Takashi Ohtsubo et al, "On-Line Analysis of Hydrogen in Molten Steel", Transaction ISIJ, vol. 25, 1985, pp. B45, B46.

Primary Examiner—Stewart J. Levy
Assistant Examiner—Joseph W. Roskos
Attorney, Agent, or Firm—Bacon & Thomas

[57] ABSTRACT

Apparatus for determining the concentration of a selected gas, e.g. hydrogen, nitrogen or oxygen, in molten metal of known temperature and composition (other than dissolved gases) comprises a tubular probe having an outer sheath, impermeable to the metal, constructed from a gas permeable refractory or cermet for immersion in the melt, a passageway for passing a gas of known composition through the probe such as to realize an equilibrium condition, via the sheath, with the gas dissolved in the melt and an analyzer for analyzing the equilibrated gas collected from the probe whereby to determine the concentration of the selected gas in the melt.

11 Claims, 1 Drawing Sheet

MOLTEN METAL GAS ANALYSIS

This invention relates to apparatus for the determination of gases which exist in molten metal, and particularly relates to measuring the concentration of eg. hydrogen, nitrogen or oxygen in molten steel.

Such gases all have to be determined in good steelmaking practice. From a practical standpoint however the speed and accuracy achieved is often less than desired. For example, for hydrogen it is difficult to obtain reproducible results on a routine basis. For oxygen the accuracy obtained hitherto is not very good at low levels, say less than 20 ppm, and this is the region which is of interest when deoxidation with aluminium is being studied. Further, oxygen probes are expensive. Nitrogen is not so much of a problem to determine but sampling and analysis thereof can be a source of delay when steels are being made to a nitrogen specification.

It is an object of this invention to provide an improved apparatus for such determination of gases.

The present invention provides apparatus for determining the concentration of a selected gas in molten metal of known temperature and composition (other than dissolved gases), comprising a tubular probe having an outer sheath impermeable to the metal constructed from a gas porous or gas permeable refractory or cermet for immersion in the melt, means for passing a gas of known composition through the probe such as to realise an equilibrium condition, via the sheath, with the gas dissolved in the melt and means for analysing the equilibrated gas collected from the probe whereby to determine the concentration of the selected gas in said melt.

The gases being determined may be hydrogen, nitrogen and oxygen; with hydrogen the probe preferably has a non porous cermet sheath. The 'input' gas will comprise a proportion of the same gas as that being determined together with an inert gas, e.g. argon or helium, to add sufficient bulk.

The gas analyses may be by any conventional unit e.g. a gas chromathograph, a thermal conductivity cell or a mass spectrometer.

Preferably, the content of the non-inert element of the input gas is chosen to be close to the expected equilibrium value to minimise the reaction time.

The principle of operation of this invention relies on the following:

The three gases chosen, dissolved in steel, are in equilibrium with the gas phase with which it is in contact according to the reactions:

$2H = H_2$

$C + O = CO$

$2N = N_2$

Measurement of the equilibrium concentrations in the gas phase therefore allows the concentrations in the steel to be calculated. This requires:
  (i) the creation of a sample of gas in equilibrium with the steel
  (ii) analysis of the gas sample
  (iii) calculation of the concentration of the dissolved gases allowing for the effects of temperature and composition.

The first condition above is met by a suitable design of probe, condition (ii) is achieved by use of conventional analytical methods and (iii) is readily determined from known gas/metal equilibrium constraints and the known relationships between activity coefficients and concentrations.

Considering in particular, the determination of the hydrogen content in steel the equilibrium of hydrogen between the 'input' gas and the hydrogen in the molten steel occurs rapidly but the attainment of equilibrium will be accelerated by replacing the inert input gas, e.g. argon, with an argon/hydrogen mixture. The closer the hydrogen content of this injected gas to the equilibrium value the quicker the equilibration process. Clearly, if the gas mixture were the same as the equilibrium value for the hydrogen content of the steel there would in fact be no difference between the compositions of the probe input and output gas. Thus, if the analysis method adopted is dependent on seeking a 'null' point the equilibration time will be zero. Likewise it will be appreciated that if for a given hydrogen-in-steel content the hydrogen content of the input gas were higher than the equilibrium value the output gas would contain less hydrogen, i.e. a hydrogen loss to the steel. Contrariwise, with the hydrogen concentration in the injected gas less than the equilibrium value hydrogen would be removed from the steel resulting in higher concentrations of hydrogen in the output gas as compared with the injected composition.

In order that the invention may be fully understood one embodiment thereof will now be described by way of example with reference to the accompanying drawings in which.

Figure 1:
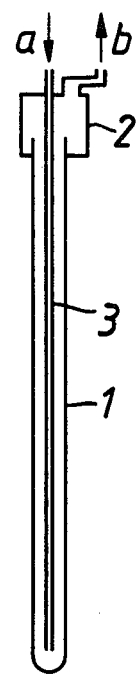
FIG. 1 illustrates the probe.

The probe shown in FIG. 1 comprises a cermet sheath 1 sealed to and dependent from a gas directing system 2, a gas inlet tube 3 e.g. a cermet or other high temperature resistant material, extending through this system and axially along the length of the sheath, exiting adjacent its remote end. Care must be taken to maintain the probe dry to eliminate hydrogen pick-up from this source.

Figure 2:
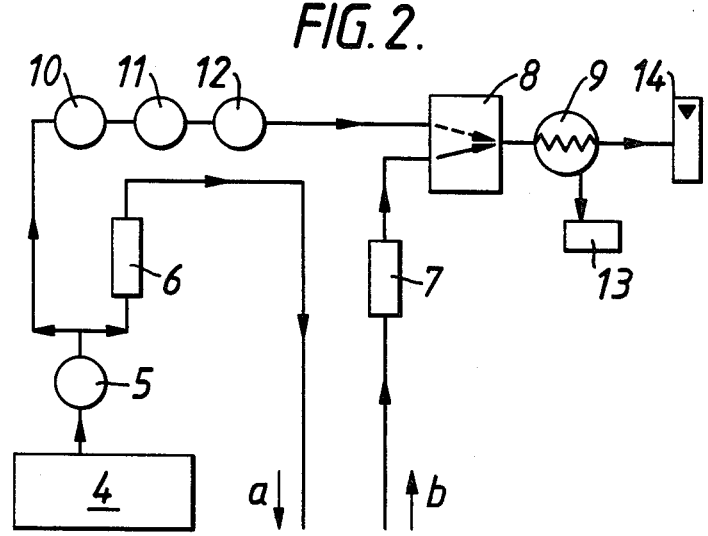
FIG. 2 illustrates the associated control and analytical equipment of this invention.

The equipment in FIG. 2 comprises a source 4 for the injected gas which is applied at a desired pressure (pressure gauge 5) via a flowmeter 6 to the probe. Typical gas compositions would be 1.2% hydrogen in argon and 2.3% hydrogen in argon chosen to equilibrate with hydrogen levels likely to be found in the steel sampled (1.2% corresponds to 3 ppm and 2.3% corresponds to 4 ppm). The output from the probe passes through a flowmeter 7 and a gas flow director 8 to an analyser 9, in this instance a katharometer.

The katharometer is calibrated empirically against the gas mixture source 4 which is applied, with the switch in the director 8 in the alternative position, via a pressure regulator 10, gauge 11 and flow control valve 12. The output of the analyser cell is indicated on a chart recorder or other display device 13, a flowmeter 14 being provided to verify the gas flow.

In one typical application the gas flow director is switched into its 'calibrate' mode and the analyser is calibrated. The probe is then inserted into the steel melt e.g. into the tundish in a continuous casting installation. The director 8 is switched into its 'measuring' mode and the output is read off at 13. This latter reading is compared with the calibration reading from which data the hydrogen content of the output gas is thereby determined. The hydrogen content of the steel is calculated from this, taking account of the temperature of the steel, and the alloying elements it contains.

Although the invention has been described with reference to the particular embodiment illustrated with reference to hydrogen detection it is to be understood that other gases may be detected and various changes may be made without departing from the scope of this invention. For example, the cermet employed —molybdenum/alumina —may be differently formulated and indeed the outer sheath may simply comprise a cermet coated on a refractory body or vice versa. The probe itself could also be differently constructed e.g. in the form of a U-tube. Different gas mixtures could also be employed, thus helium could be used instead of the inert argon element. Further, molten metal other than steel may be of interest for gas determination e.g. aluminium.

Compared with probes in which the equilibrating gas is in direct contact with the molten metal the adoption of an outer sheath impermeable to molten metal and reliance on the diffusion of the hydrogen gas through the sheath offers distinct advantages in terms of gas flow control, gas pressures, cleanliness of the output gas (metallic fumes are avoided) probe life and insensitivity to depth of immersion.

We claim:

1. Apparatus for determining the concentration of a selected gas in molten metal of known temperature and composition, other than dissolved gases, comprising a tubular probe having an outer sheath, impermeable to the metal, constructed from a gas permeable cermet for immersion in the melt, gas conducting means for passing a gas of known composition within the probe such as to realise an equilibrium condition, via the sheath, with the gas dissolved in the melt and an analyser for analysing the equilibrated gas collected from the probe whereby to determine the concentration of the selected gas in said melt.

2. Apparatus according to claim 1, wherein the probe includes an inner tube coaxial with the outer sheath, the known gas being injected through said tube.

3. Apparatus according to claim 2, wherein the selected gas is a member selected from the group consisting of hydrogen, carbon monoxide and nitrogen.

4. Apparatus according to claim 3, wherein the known gas is a mixture of the relevant selected gas and an inert gas.

5. Apparatus according to claim 4, comprising a switch whereby in one position of the switch the analyser is calibrated with the known gas and in the other position the equilibrated gas is measured by the analyser.

6. Apparatus according to claim 4, wherein the cermet is molybdenum/alumina.

7. Apparatus for determining the concentration of a selected gas in molten metal of known temperature and composition, other than dissolved gases, comprising a tubular probe having an outer sheath impermeable to the metal constructed from a gas permeable refractory for immersion in the melt, gas conducting means for passing a known gas selected from the group consisting of hydrogen, carbon monoxide and nitrogen together with argon, within the probe so as to realise an equilibrium condition, via the sheath, with the gas dissolved in the melt and an analyser calibrated with said known gas for analysing the equilibrated gas collected from the probe whereby to determine the concentration of the selected gas in said melt.

8. Apparatus according to claim 7, wherein hydrogen is the selected gas.

9. A method for determining the concentration of a selected gas in molten metal of known temperature and composition, other than dissolved gases, comprising passing a gas of known composition through gas conducting means in a tubular probe having an outer sheath impermeable to the metal but permeable to said selected gas which is immersed in molten metal so as to realise an equilibrium condition via the outer sheath with the gas dissolved in the melt and the gas passing through the gas conducting the means and measuring the equilibrium concentration of said selected gas passed through the gas conducting means.

10. The method according to claim 9, wherein said selected gas is a member selected from the group consisting of hydrogen, carbon monoxide and nitrogen.

11. The method according to claim 10, wherein said gas of known composition is a mixture of the selected gas and an inert gas.

* * * * *